(12) United States Patent
Foley et al.

(10) Patent No.: US 8,416,417 B2
(45) Date of Patent: Apr. 9, 2013

(54) SURFACE IMPEDANCE IMAGING METHODS AND APPARATUSES

(75) Inventors: Kyle James Foley, Chandler, AZ (US); Nongjian Tao, Scottsdale, AZ (US)

(73) Assignee: Arizona Board of Regents for and on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 12/989,617

(22) PCT Filed: Apr. 24, 2009

(86) PCT No.: PCT/US2009/041648
§ 371 (c)(1),
(2), (4) Date: Feb. 22, 2011

(87) PCT Pub. No.: WO2009/132262
PCT Pub. Date: Oct. 29, 2009

(65) Prior Publication Data
US 2011/0136102 A1 Jun. 9, 2011

Related U.S. Application Data

(60) Provisional application No. 61/048,159, filed on Apr. 25, 2008, provisional application No. 61/051,242, filed on May 7, 2008.

(51) Int. Cl.
*G01N 21/55* (2006.01)
(52) U.S. Cl.
USPC ........................................................ 356/445
(58) Field of Classification Search ........... 356/445–448
See application file for complete search history.

(56) References Cited

U.S. PATENT DOCUMENTS

| 5,858,799 | A | * | 1/1999 | Yee et al. | 436/164 |
| 7,150,978 | B2 | | 12/2006 | Yanagawa | 435/69.1 |
| 2003/0164947 | A1 | | 9/2003 | Vaupel | 356/445 |

FOREIGN PATENT DOCUMENTS

| WO | WO 2007/046845 | 4/2007 |
| WO | WO 2009/132262 | 10/2009 |

OTHER PUBLICATIONS

Barrena, E et al. (2000) Molecular packing changes of alkanethiols monolayers on Au(111) under applied pressure. Journal of Chemical Physics 113(6): 2413-2418, Aug. 8.
Hamelin, A et al. (1983) The electrochemical double-layer on sp metal single-crystals—the current status of data. Journal of Electroanalytical Chemistry 145(2): 225-264.
Katz, E et al. (2003) Probing biomolecular interactions at conductive and semiconductive surfaces by impedance spectroscopy: Routes to impedimetric immunosensors, DNA-Sensors, and enzyme biosensors. Electroanalysis 15(11): 913-947, July.
Kotz, R et al. (1977) Electron-density effects in surface-plasmon excitation on silver and gold electrodes. Surface Science 69(1): 359-364.
Kretschmann, E. et al. (1971) Determination of optical constants of metals by excitation of surface plasmons. Zeitschrift fur Physik 241(4): 313-324. (English abstract).
Kumar, A et al. (1994) Patterning self-assembled monolayers—applications in materials science. Langmuir 10(5): 1498-1511, May.
McIntyre, JD (1973) Electrochemical modulation spectroscopy. Surface Science 37(1): 658-682.

(Continued)

*Primary Examiner* — Michael P Stafira
(74) *Attorney, Agent, or Firm* — Fulbright & Jaworski L.L.P.

(57) ABSTRACT

Methods and apparatuses for imaging surface impedance.

29 Claims, 5 Drawing Sheets

OTHER PUBLICATIONS

Orlowski, R et al. (1976) Total reflection of light at smooth and rough silver films and surface plasmons. Surface Science 54(2): 303-308 Published: 1976.

PCT Examiner Blaine R. Copenheaver, WO 2009/132262 International Search Report mailed Jun. 24, 2009, 2 pages.

Peterlinz, KA et al. (1996) In situ kinetics of self-assembly by surface plasmon resonance spectroscopy. Landmuir 12(20): 4731-4740, October.

Porter, MD et al. (1987) Spontaneously organized molecular assemblies .4. Structural characterization of normal-alkyl thiol monolayers on gold by optical ellipsometry, infrared-spectroscopy, and electrochemistry. Journal of the American Chemical Society 109(12): 3559-3568, Jun. 10.

Tao, NJ et al. (1999) High resolution surface plasmon resonance spectroscopy. Review of Scientific Instruments 70(12): 4656-4660, December.

Wang, S et al. (2000) High sensitivity stark spectroscopy obtained by surface plasmon resonance measurement. Analytical Chemistry 72(17): 4003-4008, Sep. 1.

* cited by examiner

SURFACE IMPEDANCE IMAGING METHODS AND APPARATUSES

CROSS REFERENCES TO RELATED APPLICATIONS

This application is a national phase application under 35 U.S.C. §371 of International Application No. PCT/US2009/041648 filed Apr. 24, 2009, which claims priority to U.S. Provisional Patent Application 61/048,159, filed Apr. 25, 2008, and to U.S. Provisional Patent Application 61/051,242, filed May 7, 2008, all of which are incorporated by reference in their entireties.

The invention was made with United States government support under grant number CHM-0554786 awarded by the National Science Foundation (NSF) and under grant number NIH 1 U01 ES016064-01 awarded by the National Institutes of Health (NIH). The United States government has certain rights in the invention.

BACKGROUND OF THE INVENTION

A. Field of the Invention

A new detection principle that can image surface impedance and determine the mass to charge ratio of molecules in liquid phase and in microfluidic/nanofluidic devices.

B. Description of Related Art

Interfacial impedance spectroscopy has been widely used as a powerful technique to study various surface and electrochemical processes including electrode corrosions, electroplating and molecular adsorption and reactions. It has also been applied to chemical sensors, DNA chips, biosensors and study of cells (Katz & Willner, 2003). To date, interfacial impedance spectroscopy has been performed on a single electrode or an array of electrodes in which each electrode is individually connected to a measurement circuit. For many applications, it is highly desired to image or map the local impedance of the entire surface of an electrode, which so far has not been demonstrated. Atomic force microscopy has been used to probe local capacitance, but it rarely used for practical and routine analysis because it is slow and complicated.

To use molecular recognition for sensor applications, one has to be able to convert a molecular binding event into a signal. Based on the signal transduction mechanisms, sensors have been divided into electrical, electrochemical, optical and mechanical sensors. A good signal transduction method must be fast and sensitive, but it also highly desired to provide specific signature of the target molecules. To date, most detection principles detect a change in e.g., mass or current, associated with a molecular binding event but not capable to provide the signature or identity of the target molecule. One exception is mass spectroscopy (MS) which detects the mass to charge ratios of analytes. Since the ratio is rather unique for a molecule or fragment of molecules, MS has become a powerful method for detecting and identifying chemical species. However, MS does not work in solution phase, and miniaturization of MS for gas phase analysis faces many challenges.

SUMMARY OF THE INVENTION

The present invention overcomes deficiencies in the art as described below, and provides a new detection principle that can image or probe local surface impedance of an electrode, and determine the mass to charge ratio of molecules in liquid phase and in microfluidic/nanofluidic devices. In addition to imaging surface impedance of a bare electrode or molecules adsorbed on the electrode in real time, it also allows us to monitor molecular binding processes without using labels, which is particularly useful for biochips and biosensors. Finally, the technique can determine and image the charge of molecules adsorbed on a sensor surface, which can provide additional identity of molecules and new insights into the functions of the molecules.

The inventors demonstrated a method to image surface impedance of an electrode in solution based on the sensitive dependence of surface plasmon resonance (SPR) on local surface charge density. By applying a potential modulation to a sensor surface, the inventors are able to obtain an image of the DC component, and both the amplitude and phase images of the AC component. The DC image provides local binding and coverage of molecular adsorbates, as found in conventional SPR imaging techniques. The AC images are directly related to the local impedance of the sensor surface, which not only gives rise to better contrast than the conventional SPR images but additional local impedance spectroscopy information. Their experimental data can be quantitatively analyzed in terms of the simple free electron gas model for the sensor surface and the Randle model of the interfacial impedance.

The inventors method is based on surface plasmon resonance (SPR) detection and imaging. FIG. 1 conceptually illustrates one example of a prior art SPR imaging configuration. In a typical SPR setup, a p-polarized collimated beam from a laser or a light emitting diode (LED) is incident upon a thin metal film (sensor or electrode) through a prism, and light reflected from the metal film is detected by an imaging device. At an appropriate incident angle (called resonance angle), light excites collective oscillations of conduction electrons in the metal film, known as surface plasmons, which causes a sharp decrease in the reflection of light. SPR is sensitive to molecular binding taking place on or near the metal film, and the resonance shift is directly proportional to the mass and coverage of the molecules bound to the surface. In studies, the inventors have found that the resonance angle shift, $\Delta\theta_R$, is sensitive to the surface charge, $\Delta\sigma$ and given by, $\Delta\sigma = \alpha \Delta\theta_R$ where $\alpha$ is about 28 $C.m^{-2}deg^{-1}$. The current SPR setup can detect at $10^{-4}$ deg angular shift, which allows us to detect 2.8 $mC/m^2$. For 25% coverage of proteins, this sensitivity can detect 1-2 electron charge for a typical protein with a diameter of ~5 nm. Further improvement of the angular resolution is possible to achieve even better charge sensitivity.

Since SPR measures both mass and charge, one must separate the two in order to determine charge to mass ratio of a particular protein. One way to achieve this is to vary the pH of the buffer solution. Depending on the pH of the buffer, proteins may have different charges, which can be used to identify the proteins. At the isoelectric point, the SPR signal gives the mass of the protein. Changing the pH will result in a charged protein and the change in the SPR signal corresponds to the charge of the protein. By imaging a sensor surface at different pH, one can then plot the SPR signal of each protein vs. pH, which provides mass and charge information about the protein. The most efficient way to change pH is to use a microfluidic setup, and buffer solutions with different pH values can be automatically introduced and the SPR images at different pH values are acquired and analyzed.

Some embodiments of the present methods of imaging surface impedance, comprise: providing a sample block having a surface that is coated with a metal film; disposing a solution in contact with the metal film; providing a first electrode in contact with the solution and spaced apart from the metal film; activating a light source configured to provide light that excites Surface Plasmon Resonance (SPR) of the metal film; applying a modulated potential between the metal film and the first electrode; capturing a sequence of images of the SPR of the metal film; and time correlating the sequence of images to the modulated potential to determine the response of the SPR of the metal film to the modulated potential. Some embodiments further comprise: generating an image of an amplitude component of the AC response of the SPR and an image of a phase component of the AC response of the SPR. As used in this disclosure, the AC response or AC component are the response or component resulting from or attributable to the modulation (e.g., alternation) of the modulated potential. Some embodiments further comprise: generating an image of the DC response of the SPR. Some embodiments further comprise: generating an image of the surface impedance of the metal film from the AC response of the SPR of the metal film to the modulated potential.

In some embodiments of the present methods, the sample block is at least partially transparent to light from the light source. In some embodiments, the SPR of the metal film is excited using a Kretschmann configuration. In some embodiments, the SPR of the metal film is excited using an Otto configuration. In some embodiments, the metal film comprises an ordered pattern, and where the SPR of the metal film is excited using an optical grating configuration.

Some embodiments of the present methods further comprise: providing a second electrode in contact with the solution; where, when applying the modulated potential, the first electrode acts as a reference electrode, the second electrode acts as a counter electrode, and the metal film acts as a working electrode. In some embodiments of the present methods, the potential of the modulated potential is selected with a potentiostat. In some embodiments, the modulated potential comprises an oscillating potential superimposed on a predetermined potential value. Some embodiments of the present methods further comprise: selecting a potential with a potentiostat; and modulating the selected potential with a function generator.

In some embodiments of the present methods, the light source comprises one or more light-emitting diodes (LEDs). In some embodiments, the light source comprises a laser. In some embodiments, the light source comprises a super-luminescence diode (SLD).

In some embodiments of the present methods, the sequence of images is captured with a charge-coupled device (CCD) detector. In some embodiments, the sequence of images is captured with a complementary metal-oxide semonductor (CMOS) detector.

In some embodiments of the present methods, an analyte is adsorbed on the metal film. In some embodiments, the analyte is adsorbed on the metal film before the solution is disposed in contact with the metal film. In some embodiments, the solution comprises the analyte and where the analyte adsorbs on the metal film from the solution. In some embodiments, the analyte is a biologically relevant molecule. In some embodiments, the analyte is selected from the group consisting of: cells, bacteria, and viruses. In some embodiments, the solution comprises an electrolyte. In some embodiments, the metal film comprises gold.

Some embodiments of the present apparatuses for imaging surface impedance, comprise: a sample support configured to support a sample block having a surface that is coated with a metal film, the sample support configured to support a sample block such that a solution can be disposed in contact with the metal film of the sample block; a light source configured to provide light that can excite Surface Plasmon Resonance (SPR) of the metal film of a supported sample block; a first electrode configured to be disposed in contact with a solution and spaced apart from the metal film of a supported sample block; a modulated potential source coupled to the first electrode and configured to be coupled to the metal film of a sample block such that the modulated potential source is activatable to provide a modulated potential between the metal film and the electrode; an imaging device configured to capture a sequence of images of SPR of the metal film of a supported sample block; a processor coupled to the modulated potential source and to the imaging device, the processor configured to receive a sequence of images of SPR of the metal film of a supported sample block and to determine the response of the SPR of the metal film to the modulated potential by time correlating the sequence of images to the modulated potential.

In some embodiments of the present apparatuses, the processor is further configured to generate an image of an amplitude component of the AC response of the SPR and an image of a phase component of the AC response of the SPR. In some embodiments, the processor is further configured to generate an image of the DC response of the SPR. In some embodiments, the processor is further configured to generate an image of the surface impedance of the metal film from the AC response of the SPR of the metal film to the modulated potential.

In some embodiments of the present apparatuses, the sample block is at least partially transparent to light from the light source. In some embodiments, the apparatus is configured to support a sample block and to excite SPR of the metal film of a supported sample block in a Kretschmann configuration. In some embodiments, the apparatus is configured to support a sample block and to excite SPR of the metal film of a supported sample block in an Otto configuration. In some embodiments, the apparatus is configured to support a sample block on which the metal film comprises an ordered pattern, and where the apparatus is configured to excite SPR of the metal film of a supported sample block in an optical grating configuration.

Some embodiments of the present apparatuses further comprise: a second electrode coupled to the modulated potential source and configured to be disposed in contact with a solution and spaced apart from the metal film of a supported sample block; where, if the modulated potential source is activated to apply a modulated potential between the first electrode and the metal film of a supported sample block, the first electrode acts as a reference electrode, the second electrode acts as a counter electrode, and the metal film acts as a working electrode.

In some embodiments of the present apparatuses, the modulated potential source comprises a potentiostat configured to select the value of a modulated potential to be applied by the modulated potential source. In some embodiments, the modulated potential source comprises a signal generator to modulate the selected potential value. In some embodiments, the modulated potential source is configured to provide apply an oscillating potential superimposed on a selected potential value.

In some embodiments of the present apparatuses, the light source comprises one or more light-emitting diodes (LEDs). In some embodiments, the light source comprises a laser. In some embodiments, the light source comprises a super-luminescence diode (SLD).

In some embodiments of the present apparatuses, the imaging device comprises a charge-coupled device (CCD) detector. In some embodiments, the imaging device comprises a complementary metal-oxide semonductor (CMOS) detector.

It is contemplated that any embodiment discussed in this specification can be implemented with respect to any method or system of the invention, and vice versa. Furthermore, systems of the invention can be used to achieve methods of the invention.

The term "about" or "approximately" are defined as being close to as understood by one of ordinary skill in the art, and in one non-limiting embodiment the terms are defined to be within 10%, preferably within 5%, more preferably within 1%, and most The term "effective," as that term is used in the specification and/or claims, means adequate to accomplish a desired, expected, or intended result.

The use of the word "a" or "an" when used in conjunction with the term "comprising" or other open-ended language in the claims and/or the specification means "one or more."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

Figure 1:
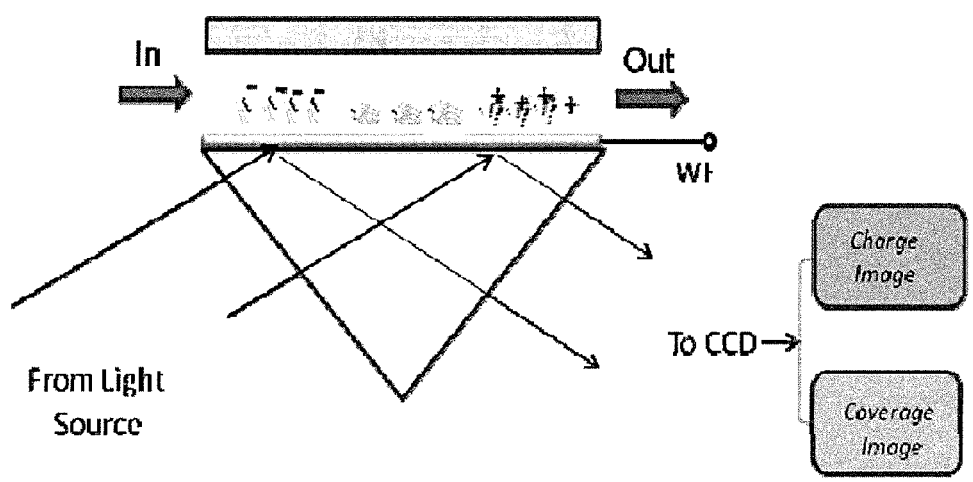
FIG. 1 illustrates one example of a prior art SPR imaging configuration.

The basic principle of the inventors technique is that SPR is sensitive to the surface charge density of a metal film (McIntyre, 1973; Kotz et al., 1977). In a typical SPR imaging setup, a p-polarized collimated beam from a laser or a light emitting diode (LED) is incident upon a thin metal film through a prism, and light reflected from the metal film is detected by an imaging device (FIG. 2A). At an appropriate incident angle (resonance angle), light excites collective oscillations of conduction electrons in the metal film, known as surface plasmons, which causes a sharp decrease in the intensity of the reflected beam. Since the resonance angle is highly sensitive to molecular binding taking place on or near the metal film, SPR has emerged as a label-free detection method in biosensors. In contrast, impedance spectroscopy is based on an entirely different principle. Interfacial differential impedance is defined by $Z=\Delta V/\Delta I$, where $\Delta V$ is a potential modulation applied to an electrode and $\Delta I$ is current modulation as a result of the potential modulation. Since $\Delta I$ usually has a different phase from $\Delta V$, Z is described by a complex number (or amplitude and phase). Z is very sensitive electrode surface and molecular adsorption taking place on the electrode surface, which is basis of impedance spectroscopy for studying interfacial phenomena and biosensors.

SPR provides a sensitive measurement of the impedance at the metal-liquid interface if one applies a potential modulation of the SPR sensor surface, just like impedance analysis. The potential modulation causes a surface charge modulation which changes the surface plasmons in the metal film. By measuring the amplitude and phase of the resonance angle, the inventors can obtain interfacial impedance information. Since the inventors can measure small changes in the resonance angle, the impedance can be determined accurately. Even more importantly, by operating SPR in imaging mode the inventors can obtain an image of the impedance of the entire electrode surface.

By measuring SPR in an electrolyte, the inventors obtain interfacial impedance by applying a potential modulation to the sensor surface. This is because the potential modulation causes a surface charge modulation which changes the surface plasmons in the metal film. By measuring the amplitude and phase of the resonance angle, one can obtain interfacial impedance information. The inventors have demonstrated before that a modulation in the resonance angle smaller than $10^{-6}$ deg can be measured, so accurate imaging of surface impedance is possible based on SPR detection (Wang et al., 2000).

A quantitative relation between SPR angle modulation and interfacial impedance can be derived based on the following steps. First, it has been found that the resonance angle, $\theta_R$, is related to the dielectric constant of the metal film, $\in_m$, according to $$\sin(\theta_R) = \sqrt{\frac{\varepsilon_1 \varepsilon_m}{(\varepsilon_1 + \varepsilon_m)\varepsilon_2}} \quad (1)$$

where $\in_1$ and $\in_2$ are the dielectric constants of the buffer solution and prism, respectively (Orlowski & Raether, 1976).

$\epsilon_m$ depends on the surface charge density, which is the reason that the SPR resonance angle is sensitive to the surface charge density. An explicit relationship between $\epsilon_m$ and surface charge density can be obtained based on the Drude model, a free electron gas model for metals (Kittel, 2005). According to the Drude model, $\epsilon_m$ of the metal film as a function of frequency, f, is given by $$\varepsilon_m(f) = 1 - \frac{n_e e^2}{\varepsilon_0 m_e 4\pi^2 f^2} \quad (2)$$

where e, $m_e$, and $n_e$ are the electron charge, mass, and density, respectively, and $\epsilon_o$=8.85×10$^{-12}$ F/m. For a thin metal film of thickness $d_m$, a change in the surface charge, $\Delta\sigma$, gives rise to a change in the electron density and thus the dielectric constant of the metal, according to (3)

$$\Delta\sigma = -e d_m \Delta n_e \quad (3)$$

Substitute Eq. 2 into Eq. 3, and one can express the charge density change in terms of the metal dielectric constant change $$\Delta\sigma = -\frac{e d_m n_e}{\varepsilon_m - 1} \Delta\varepsilon_m \quad (3')$$

Combining Eqs. 1 and 3', the inventors find that a surface charge change, $\Delta\sigma$, causes a linear change in the resonance angle, $\Delta\theta_R$ according to $$\Delta\sigma = \alpha \Delta\theta_r, \quad (4)$$

where $$\alpha = -\frac{e d_m n_e \varepsilon_2 (\varepsilon_1 + \varepsilon_m)^2 \sin(2\theta_R)}{\varepsilon_1^2 (\varepsilon_m - 1)} \quad (5)$$

In the present experiment, $\epsilon_1$=1.77 (water), $\epsilon_2$=2.29 (BK7 prism), $d_m$=47 nm, $n_e$=5.9×10$^{-28}$ m$^{-3}$ and $\epsilon_m$=−11.7 for the Au film, $\theta_R$=72° according to Eq. 1, and $\alpha$=28 C.m$^{-2}$deg$^{-1}$. Finally since surface charge density is related to interfacial capacitance density (capacitance per unit area), c, by $$\Delta\sigma = c\Delta V \quad (6)$$

where $\Delta V$ is the surface potential change which can be modulated and controlled using a standard electrochemical setup. One can image the interfacial capacitance by monitoring local SPR response as a result of applied potential modulation by $$c(x,y) = \alpha \Delta\theta_R(x,y)/\Delta V \quad (7)$$

The above analysis establishes a simple relation between potential-modulated local SPR and local interfacial capacitance, which is the basic principle of the inventors interfacial impedance imaging technique. As discussed below, the Drude model provides a semi-quantitative description of experimental data. When the Drude free electron gas model is replaced by a more sophisticated theory, the conclusion still holds except that $\alpha$ is replaced by a more accurate number.

One assumption used in deriving the above relation is that the resistance of the electrolyte or buffer solution is negligible. While this assumption is reasonable in many cases, a more complete model (e.g. Randles equivalent circuit model [Bard & Faulkner, 2001]) treats the metal-solution interface by a capacitor, C, in parallel with a resistor, R, and the solution phase resistance by a resistor, $R_s$ FIG. 1B). As the inventors will discuss later, this extra resistance introduces a phase shift between the resonance angle modulation, $\Delta\theta_R(x,y)$, and the potential modulation, $\Delta V$. In this case, the one can obtain both amplitude and phase images of the surface.

APPARATUS

Figure 2:
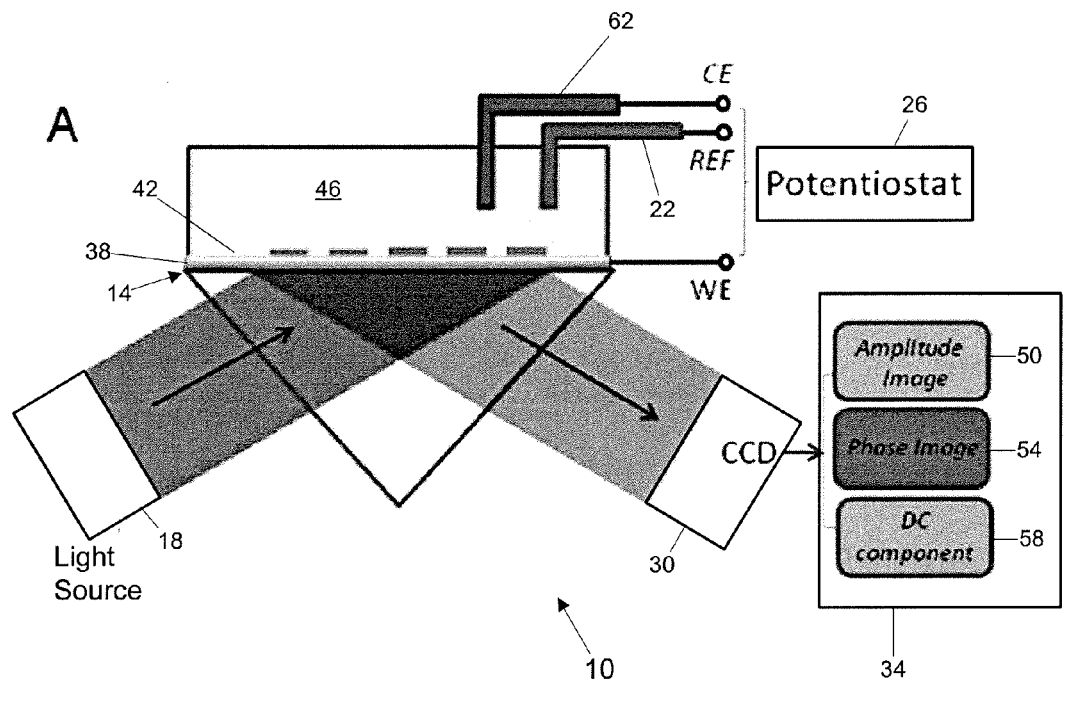
FIG. 2A and FIG. 2B: (A) Schematic of apparatus for imaging surface impedance (experimental setup) and (B) equivalent circuits used in modeling surface impedance showing the Randles equivalent circuit (left) and the two-component model with parallel resistor and capacitor (right).
Figure 2:
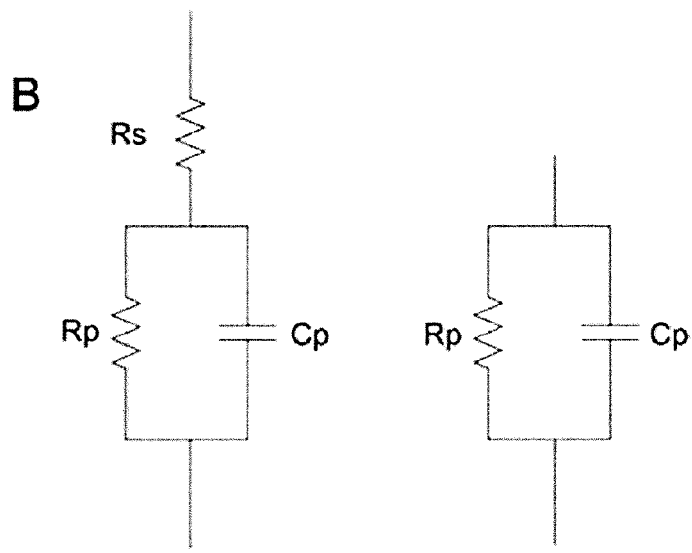

FIG. 2 depicts an example of an apparatus 10 for imaging surface impedance. In the embodiment shown, apparatus 10 comprises: a sample support 14, a light source 18, a first electrode 22, a modulated potential source 26, an imaging device 30, and a processor 34. Sample support 14 is configured to support a sample block (e.g., 38) having a surface that is coated with a metal film 42. The sample support is configured to support a sample block (e.g., 38) such that a solution (e.g., 46) can be disposed in contact with the metal film (e.g., 42) of the sample block. Light source 18 is configured to provide light that can excite Surface Plasmon Resonance (SPR) of the metal film (e.g., 42) of a supported sample block (e.g., 38). First electrode 22 is configured to be disposed in contact with a solution (e.g., 46) and spaced apart from the metal film (e.g., 42) of a supported sample block (e.g., 38). Modulated potential source 26 is coupled to first electrode 22 and configured to be coupled to the metal film (e.g., 42) of a sample block (e.g., 38) such that the modulated potential source is activatable (can be activated) to provide a modulated potential between the metal film (e.g., 42) and the first electrode (e.g., 22). Imaging device 30 is configured to capture a sequence of images of SPR of the metal film (e.g., 42) of a supported sample block (e.g., 38). Processor 34 is coupled to modulated potential source 26 and to imaging device 30, and is configured to receive a sequence of images of SPR of the metal film (e.g., 42) of a supported sample block (e.g., 38) and to determine the response of the SPR of the metal film to the modulated potential by time correlating the sequence of images to the modulated potential (e.g., by way of the principles and methods described in this disclosure).

In the embodiment shown, processor 34 is further configured to generate an image 50 of an amplitude component of the AC response of the SPR and an image 54 of a phase component of the AC response of the SPR. In the embodiment shown, processor 34 is also further configured to generate an image 58 of the DC response of the SPR. In the embodiment shown, processor 34 is further configured to generate an image of the surface impedance of the metal film from the AC response of the SPR of the metal film to the modulated potential, such as, for example, using the principles, models, and methods described in this disclosure. Processor 34 can be configured to perform any of the various functions or method steps described in this disclosure, such as, for example, by way of suitable (e.g., computer executable) program code and/or instructions, that can be embodied in tangible computer-readable media such as CD-ROM, DVD-ROM, flash drives, hard drives, or other memory (not shown), or the like that can be coupled to processor 34.

In the embodiment shown, sample block 38 is at least partially transparent to light from the light source. In the embodiment shown, apparatus 10 is also configured to support a sample block (e.g., 38) and to excite SPR of the metal film of a supported sample block in a Kretschmann configuration. In other embodiments, the apparatus can be configured to support a sample block and to excite SPR of the metal film of a supported sample block in an Otto configuration. In some embodiments, the apparatus can be configured to support a sample block on which the metal film comprises an ordered pattern such that the apparatus can be configured to excite SPR of the metal film of a supported sample block in an optical grating configuration.

In the embodiment shown, apparatus 10 further comprises a second electrode 62 coupled to modulated potential source 26 that is configured to be disposed in contact with a solution (e.g., 46) and spaced apart from the metal film (e.g., 42) of a supported sample block (e.g., 38. In this way, if (and/or when) modulated potential source 26 is activated to apply a modulated potential between first electrode 22 and the metal film (e.g., 42) of a supported sample block (e.g., 38), first electrode 22 acts as a reference electrode, second electrode 62 acts as a counter electrode, and the metal film (e.g., 42) acts as a working electrode.

In the embodiment shown, modulated potential source 26 comprises a potentiostat configured to select the value of a modulated potential to be applied by the modulated potential source. In the embodiment shown, modulated potential source 26 further comprises a signal generator to modulate the selected potential value. In this way, modulated potential source 26 can be configured to provide apply an oscillating potential superimposed on a selected potential value.

In the embodiment shown, light source 18 comprises one or more light-emitting diodes (LEDs). In other embodiments, light source 18 can comprise a laser, a super-luminescence diode (SLD) (e.g., one or more SLDs), and/or any other suitable components (e.g., one or more polarizing lenses, one or more collimating lenses, and/or the like). In the embodiment shown, imaging device 30 comprises a charge-coupled device (CCD) detector. In other embodiments, imaging device 30 can comprise a complementary metal-oxide semonductor (CMOS) detector.

Certain embodiments of the present methods can be performed with various embodiments of the apparatus 10 of FIG. 2. In one embodiment, a method of imaging surface impedance, comprises: providing a sample block (e.g., 38) having a surface that is coated with a metal film (e.g., 42); disposing a solution (e.g., 46) in contact with the metal film 42; providing a first electrode (e.g., 22) in contact with the solution 46 and spaced apart from the metal film 42, as shown; activating a light source (e.g., 18) configured to provide light that excites Surface Plasmon Resonance (SPR) of the metal film 42; applying a modulated potential between the metal film 42 and the first electrode 22 (e.g., by way of modulated potential source 26); capturing a sequence of images of the SPR of the metal film 42 (e.g., by way of imaging device 30); and time correlating the sequence of images to the modulated potential to determine the response of the SPR of the metal film to the modulated potential (e.g., by way of processor 34).

In some embodiments, the method can further comprise generating (e.g., by way of processor 34) an image (e.g., 50) of an amplitude component of the AC response of the SPR and an image (e.g., 54) of a phase component of the AC response of the SPR. In some embodiments, the method can further comprise generating (e.g., by way of processor 34) an image (e.g., 58) of the DC response of the SPR. In some embodiments, the method can further comprise generating (e.g., by way of processor 34) an image of the surface impedance of the metal film from the AC response of the SPR of the metal film to the modulated potential.

In some embodiments, the method further comprises providing a second electrode (e.g., 62) in contact with the solution 46; where, when applying the modulated potential, the first electrode 22 acts as a reference electrode, the second electrode 62 acts as a counter electrode, and the metal film 42 acts as a working electrode. In some embodiments, an analyte is adsorbed on the metal film 42 (e.g., before the solution is disposed in contact with the metal film). In some embodiments, the solution 46 comprises the analyte and the analyte adsorbs on the metal film 42 from the solution 46. The analyte can be, for example, a biologically relevant molecule, and can be selected from the group consisting of: cells, bacteria, and viruses. In some embodiments, the solution 46 comprises an electrolyte. In some embodiments, the metal film 42 comprises gold. In some embodiments of the present methods, applying the modulated potential comprises (e.g., with a modulated potential source comprising a potentiostat and a function generator): selecting a potential with a potentiostat; and modulating the selected potential with a function generator.

EXAMPLE

The SPR imaging setup (apparatus) is based on the widely used Krechmann configuration (FIG. 2A) (Kretschmann, 1971). The optics is comprised of an LED light source (670 nm) (light source 18), collimating lens, prism, imaging optics, polarizer, and a CCD camera (imaging device 30). Initially, the collimated incident beam was adjusted and then fixed at an angle where the reflectivity detected by the CCD is ~50% of the maximum intensity. A local shift in the resonance angle causes a change in the measured reflectivity which is imaged with the CCD. The SPR image was captured at up to 380 fps, allowing for measurements of the SPR response induced by the applied potential modulation. The images were recorded at a bit depth of 14 bits with a maximum resolution of 320×240 pixels. An image captured signal (square wave) was recorded from the camera to allow for synchronizing (time correlating) the image with the electrochemical current and potential data measured in concert. An electrochemical cell was made of Teflon using a silver wire as quasi reference electrode (first electrode 22) and a platinum wire as counter electrode (second electrode 62). The potential and electrochemical current were controlled and measured using a potentiostat (available from Pine Instrument Company, U.S.A.), and a sinusoidal potential modulation is applied with a function generator (available from Hewlett Packard (HP), U.S.A.) (collectively, modulated potential source 26). The modulation frequency ranged from 1 Hz up to 70 Hz at amplitude up to 100 mVpp. Typically, a total of 10,000 images were captured along with modulating potential and electrochemical current. The data collection was achieved using a personal computer (PC) (processor 34) with LabView software (available from National Instruments, U.S.A.) for voltage and current acquisition, and suitable image-capturing software for image acquisition via FireWire 800 (IEEE 1394B). Post-processing of data was accomplished using a suitable program written in MATLAB (available from The MathWorks, Inc., U.S.A.).

The SPR sensing surface (also served as the working electrode) was made of a BK7 glass cover slip (18 mm×18 mm) (sample block 38) coated with ~2 nm Chromium followed by ~47 nm gold (metal film 42). Arrays of 1-dodacanethiol (DDT) spots were created using the PDMS contact printing method to demonstrate the impedance imaging technique (Kumar et al., 1994). The PDMS stamp was first submerged in a ~10 mM thiol solution for ~5 minutes and placed onto the gold surface after drying with nitrogen gas. Then after about one minute the stamp was removed and the gold slide with the thiol pattern was placed upon the prism with refractive index matching oil between them. The electrochemical SPR cell was mounted on the gold slide and 50 mM Tris buffer (pH=8) was introduced.

Results and Discussions

The inventors carried out the initial test of the principle using a sensor on which the gold film is divided into two electrically isolated areas. The two areas were exposed to the same electrolyte and shared the same reference and counter electrodes but their potentials were independently controlled with the bipotentiostat. The current through each of the two working electrodes was monitored along with the potential throughout the SPR experiment. In order to observe the relative contrast of the two areas, the inventors coated one area with dodecanethiol (DDT) using a PDMS stamp and left the other bare. By applying an AC modulation to the potentials of the two areas, the inventors were able to measure the impedance of the two areas and image the SPR responses simultaneously.

Figure 3:
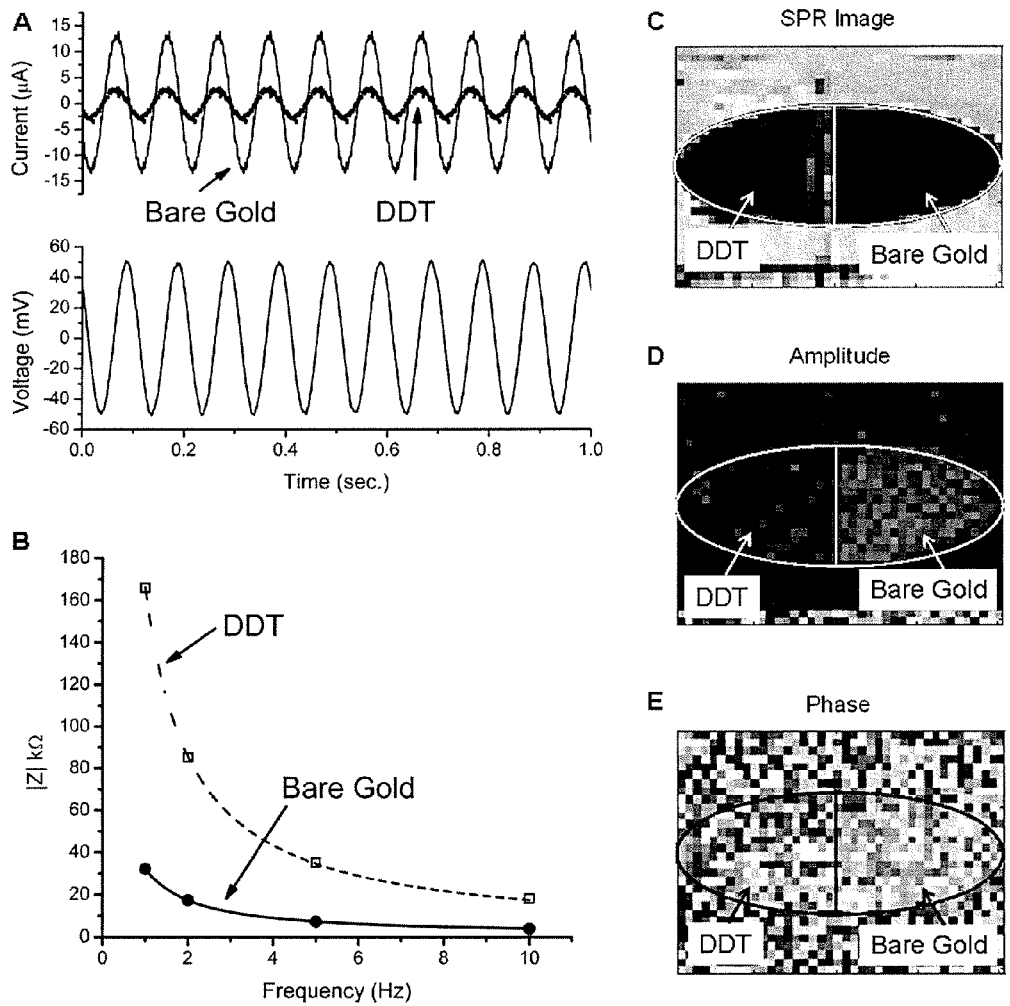
FIG. 3A, FIG. 3B, FIG. 3C, FIG. 3D, and FIG. 3E: Results from the two divided area experiments. (A) Electrochemical current modulations of the bare (larger amplitude, thin line) and DDT-covered (smaller amplitude, thick line) areas as a result of a 10 Hz modulating potential. (B) Measured (dots) and fit (lines) impedance amplitudes vs frequency for the bare (solid line) and DDT-covered (dashed line) areas. (C) DC component image of the SPR response showing contrast due to molecular adsorption. The darker region in the oval is the region exposed to solution which is divided into two areas near the center, and the lighter region (around the oval) is outside of the solution cell. (D) Amplitude (AC) image of the SPR modulation. (E) Phase (AC) image of the SPR modulation.

The inventors measured the impedance of the two areas by recording the amplitude and phase shift relative to the applied potential of the current of each area at various different frequencies and amplitudes of the potential modulations (FIG. 3A and FIG. 3B). The results were fitted using the Randle model (FIG. 2B). The fitting parameters were: $R_p$=74±20 k$\Omega$ and $C_p$=4.6±0.3 µf, for the bare gold side; and $R_p$=570±60 k$\Omega$ and $C_p$=0.92±0.01 µF for the DDT side. The interfacial resistance, $R_p$ for the DDT covered surface is much greater than that for the bare gold electrode, which is expected considering the blockade of interfacial charge transfer by the DDT layer. The interfacial capacitance, $C_p$, of the DDT surface is nearly five times smaller than that of the bare gold electrode, which is also expected due to the increased double layer thickness of the DDT covered electrode. The corresponding capacitance per unit area for the bare gold is ~47 µF/cm$^2$, which is in good agreement with literature (Hamelin et al., 1983). The capacitance per unit area for the DDT-coated surface is 9.4 µF/cm2, which is higher than reported in literature (Porter et al., 1987). This difference is possibly due to low coverage and imperfect packing of DDT layer formed by the contacting printing approach in this study. This observation is supported by the SPR data which will be discussed below. The solution resistance, $R_s$=~2 k$\Omega$, is much smaller than the interfacial charge transfer resistance. Therefore, to a first-order approximation, one can assume negligible solution resistance.

The SPR response includes a DC component in the SPR angle that provides molecular binding and adsorbate coverage and thickness information as the conventional SPR imaging technique. It contains also an AC modulation in the SPR angle resulted from the modulation of the surface potential (FIG. 3C, FIG. 3D, and FIG. 3E). The DC component is the reflectivity from the sensor surface which is linearly proportional to the resonance angle within a limited range of about 1.5 deg. The inventors determined the linear coefficient by both performing numerical simulation and experimental calibration. The simulation using Winspall, an SPR modeling program, gives a linear coefficient of 0.045 deg per 1% reflectivity change. The experimental calibration was achieved by measuring the reflectivity changes induced by injection ethanol solutions with different concentrations into the sample cell. Alternatively, one can check the intensity change by rotating the prism. FIG. 3C shows the SPR DC-component image. The reflectivity of the two areas was determined from the SPR image and they were 54.74% and 58.47%, respectively. From the contrast difference and the linear coefficient, the inventors determined that the DDT area has an average resonance angle of ~10 mdeg greater than that of the bare gold area. The difference in the resonance angles between the bare and the DDT areas corresponds to a thickness of ~1 nm if assuming the dielectric constant of 2.10 for the DDT film (Peterlinz & Georgiadis, 1996). This value is reasonable agreement with the expected thickness of the DDT monolayer. This value is smaller than the thickness of a perfectly ordered DDT monolayer (~1.4 nm) (Barrena et al., 2000), indicating an imperfect coverage of DDT as found also from the impedance measurement discussed above.

The AC component of the SPR response includes the amplitude and phase information of the reflectivity modulation induced by the surface potential modulation. The local amplitude and phase information of the sensor surface was extracted by performing Fast Fourier Transform (FFT) on each pixel of the CCD imager, which creates an amplitude image and a phase image (FIG. 3D and FIG. 3E). To improve the signal to noise ratios of the amplitude and phase images, a group of pixels can be selected and the averaged amplitude and phase information was determined to create images. This approach does sacrifice the spatial resolution, so one must optimize the spatial resolution and signal-to-noise merit according to the need of different applications. The amplitude image shows that the resonance angle modulation induced by a 0.05 V modulation in the potential is ~3×10$^{-4}$ deg, or ~9 mdeg/V, for the bare gold area. This value is slightly smaller than ~9 mdeg/V reported in literature, (Tao et al., 1999) which is possibly due to the DDT contamination of the bare gold area. Using the measured ~10 mdeg/V modulation and interfacial capacitance of 47 µF/cm$^2$, the inventors found that $\alpha_{exp}$=47 C.m$^{-2}$deg$^{-1}$, which is close to $\alpha$=28 C.m$^{-2}$deg$^{-1}$, the calculated value based on the free electron gas model.

The average modulation amplitude in the resonance angle for the DDT area is 1.3×10$^{-4}$ deg, smaller than that of the bare gold electrode. Using $\alpha_{exp}$=7.8×10$^3$ µC/cm$^2$, the inventors find the interfacial capacitance is about 12 µF/cm$^2$, which is somewhat greater than the directly measured capacitance value. Given the error bar in $\alpha_{exp}$ and the neglect of the finite resistance of the solution phase, this agreement is considered to be good. Without solution resistance, the modulation in the resonance angle should be always in phase with the applied potential modulation, and the phase image should show little contrast. As shown in FIG. 3E, the contrast of the phase image is indeed small, but not zero. The non-zero phase contrast is due to the small but finite solution phase resistance. As discussed below, the phase shift in the resonance angle increases with the modulation frequency, which can be fully described by including a finite solution phase resistance in the Randle model.

The experimentation described above show that the invention provides simultaneous SPR imaging and interfacial impedance measurement. Although local interfacial impedance information is possible by the conventional surface impedance analysis techniques using an array of individually addressed electrodes, the most attractive feature of the present method is that the local impedance can be mapped out with micron-level resolution without the need of dividing the sensor surface into individual electrically insulated electrodes. The use of an array of electrodes creates a heterogenous surface that may affect certain measurements, such as of cells, and also demands massive interconnection of electrodes to an impedance analyzer. To demonstrate the unique feature, the inventors printed an array of DDT onto a gold sensor surface using the micro-contact printing approach described in the studies section.

Figure 4:
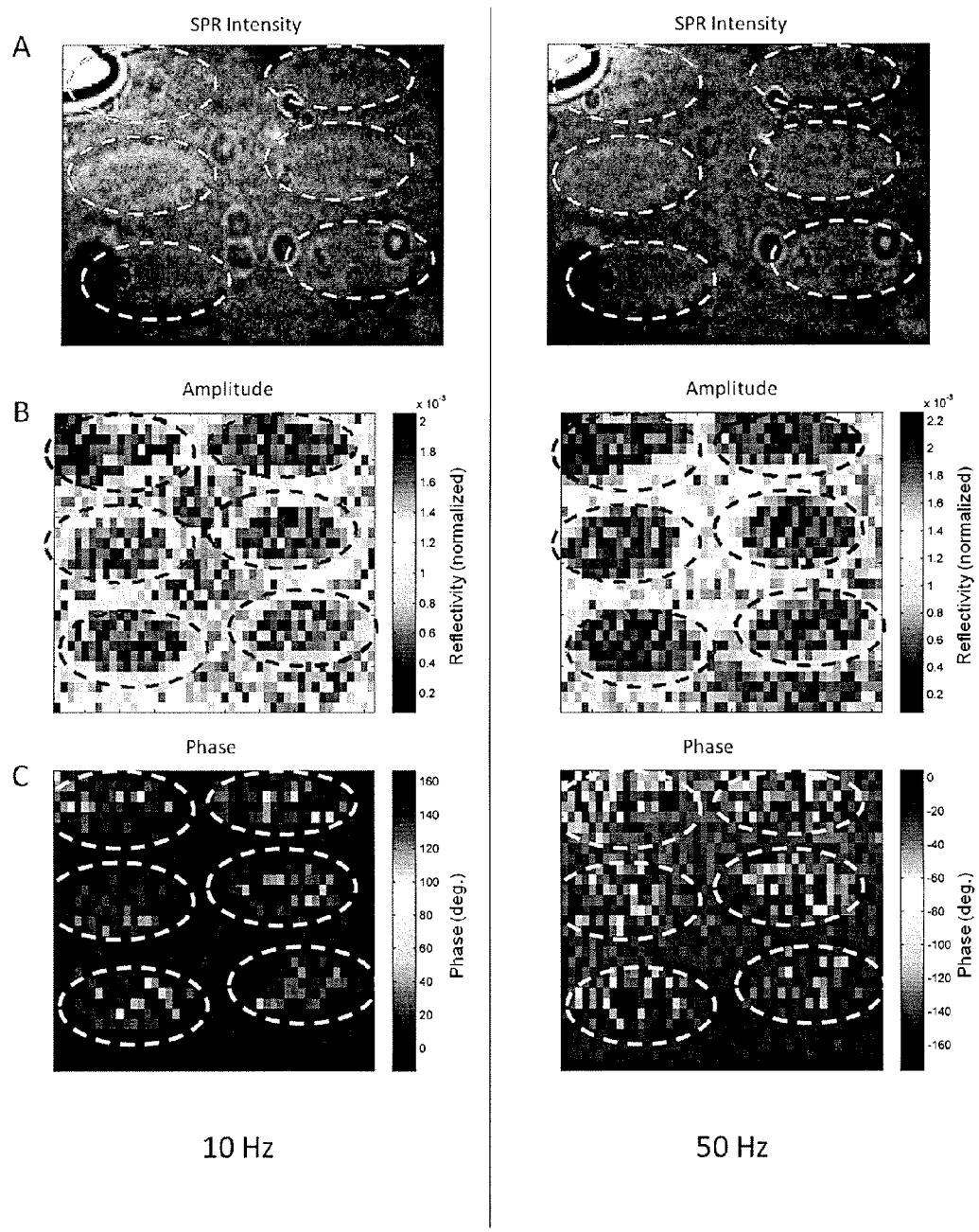
FIG. 4A, FIG. 4B, and FIG. 4C: (A) SPR image, (B) amplitude, and (C) phase images at 10 and 50 Hz. The spots were created using a PDMS stamp soaked in ~10 mM DDT solution and then placed on the gold surface for 30 s. The elliptical areas show the printed DDT regions. The contrast of the image has been changed to enhance the image.

FIG. 4A shows the DC component image of the surface which resolves a 3×2 array of DDT similar to conventional SPR imaging technique. The areas marked by ovals are covered with DDT and outside of the ovals is bare gold surface. The amplitude and phase images are shown in FIG. 4B and FIG. 4C at two different modulation frequencies. The amplitude image shows a far better contrast than the conventional SPR imaging mode (DC component), indicating a potentially a more-sensitive detection of molecular binding on surfaces. The negative contrast of the amplitude image is due to that the DDT-covered areas have smaller capacitance than the bare gold surface. The phase image shows a very small contrast of the array indicating a relatively small phase difference between the DDT-covered and bare gold surfaces. As the inventors have already discussed, in the absence of solution phase resistance, the phase image should have zero contrast and both the amplitude and phase images should not be dependent on the modulation frequency. However, a small phase contrast is observed and the amplitude contrast depends on the modulation frequency, which indicates the importance of the solution phase resistance. Using the Randle model, the inventors found that for a given applied modulation, $\Delta V_{app}$, the actual potential modulation across the metal-solution interface is given by $$\Delta V_{interface} = \frac{R_p}{R_p + R_s + j2\pi fR_pR_sC_p}\Delta V_{app} \quad (8)$$

where $C_p$ is the total capacitance of the metal-solution interface and is location-dependent (see Eq. 7). The local resonance angle is obtained by replacing $\Delta V_{app}$ in Eq. 7 with Eq. 8 and substituting in $C_p(x, y)$ in the place of $c(x, y)$ with the dependence on spatial location shown, which then takes the form of $$\Delta \theta_R(x, y) = \frac{R_pC_p(x, y)}{\alpha(R_p + R_s + j2\pi fR_pR_sC_p(x, y))}\Delta V_{app} \quad (9)$$

Figure 5:
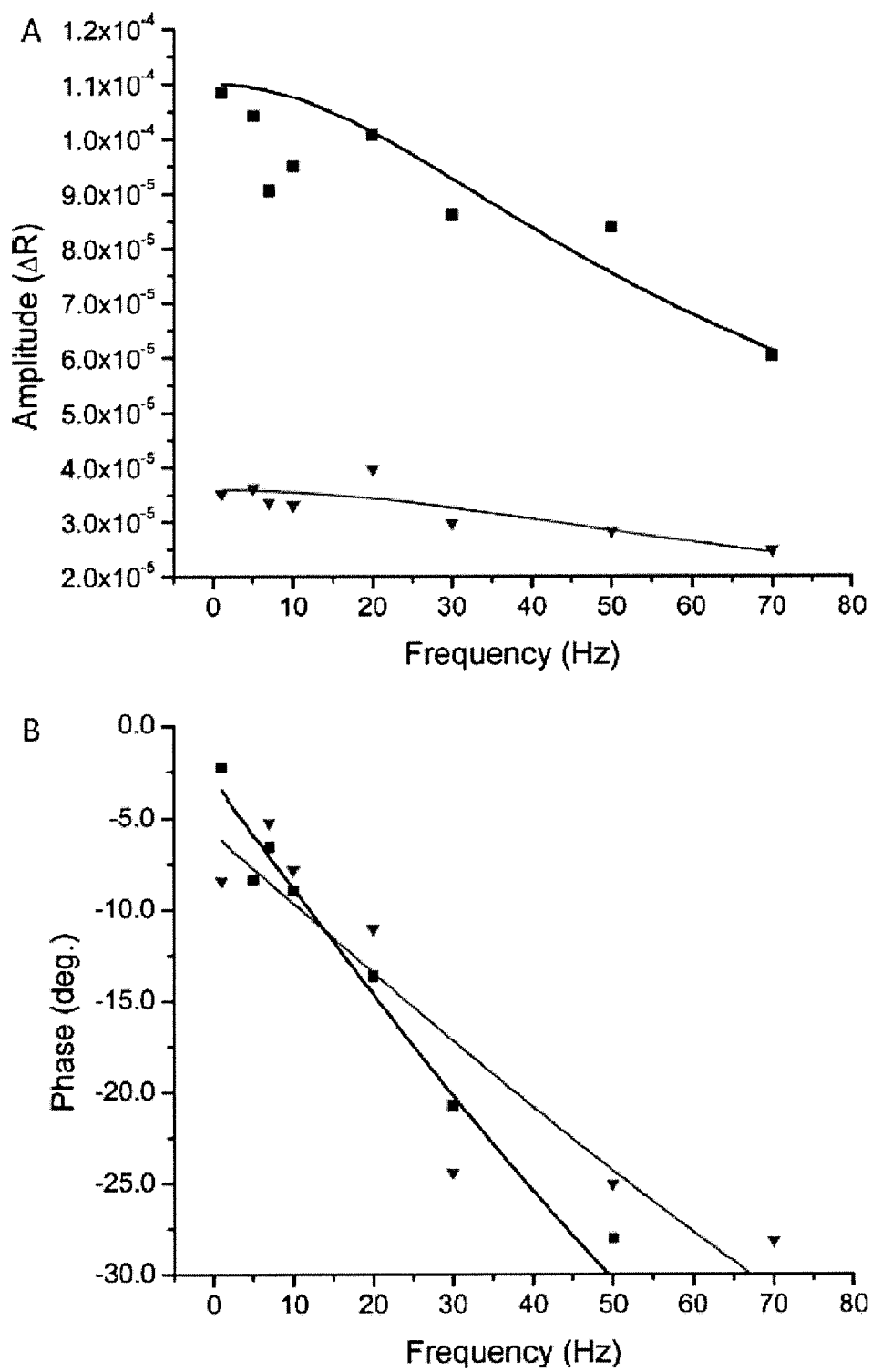
FIG. 5A and FIG. 5B: (A) Amplitude and (B) phase comparison of a DDT array element (T) and a bare gold element (S). The amplitude of the DDT element is smaller than that of the bare gold element. Extracting the capacitance values from the curve fits for the amplitude resulted in values of 50.7 $\mu F/cm^2$ for the bare gold and 12.7 $\mu F/cm^2$ for the DDT spot.

To verify the analysis, the inventors have determined the modulation amplitude and phase shift for both the bare gold surface and DDT elements (FIG. 5A and FIG. 5B). Both the amplitude and phase decrease with frequency, as predicted by the simple model. The frequency-dependent amplitude and phase can be fit with Eq. 9 using nonlinear least-squares methods with fitting parameter $\beta=(2\pi cRR_s/(R+R_s))^2=4.5\times 10^{-4}$ for the bare gold area and $2.4\times 10^{-4}$ for the DDT area. Using the low-frequency amplitude values for the bare and DDT regions, the interfacial capacitance values were equal to 50.7 and 12.7 $\mu F/cm^2$, respectively. These correspond well with the values measured in the two-area experiments described above.

The analysis shows that just like conventional impedance spectroscopy one can obtain important interfacial parameters in terms of model resistors and capacitors by performing the measurement as a function of modulation frequency. The highest possible frequency is limited by the imaging device, which is less than 1 kHz in the present case. However, 1 million frames-per-second CCDs are already commercially available, which could be expand the upper limit to ~MHz. Furthermore, the rapid development of CMOS imaging sensors will likely lead to faster and less expensive imaging devices.

CONCLUSION

The inventors have demonstrated a technique that allows us to image surface impedance in solution, which expands powerful surface impedance spectroscopy to include surface impedance microscopy. The basic principle relies on the sensitive dependence of SPR angle on surface charge density which can be modulated by applying an AC modulation to the potential of the sensor surface. Using FFT, the inventors extract the local amplitude and phase of the potential-induced modulation in the SPR angle and construct both the amplitude and phase images. The measured SPR angle modulations are in good agreement with the simple free electron gas model for the metal film (SPR sensor surface), and the frequency-dependence of the amplitude and phase images can be described by the Randle model. The DC component is the same as the conventional SPR image, which is also imaged simultaneously with the AC imaging to provide molecular binding information. In addition to providing local impedance information of the sensor surface, the AC images show better contrast which may help us to reveal features not possible with the conventional SPR imaging techniques.

All of the systems and/or methods disclosed and claimed in this specification can be made and executed without undue experimentation in light of the present disclosure. While the systems and methods of this invention have been described in terms of preferred embodiments, it will be apparent to those of skill in the art that variations may be applied to the systems and/or methods and in the steps or in the sequence of steps of the method described herein without departing from the concept, spirit and scope of the invention. More specifically, it will be apparent that other types of equipment may be substituted for the specific equipment types described herein while the same or similar results would be achieved. All such similar substitutes and modifications apparent to those skilled in the art are deemed to be within the spirit, scope and concept of the invention as defined.

REFERENCES

The following references, to the extent that they provide exemplary procedural or other details supplementary to those set forth herein, are specifically incorporated herein by reference.

Bard, A. J.; Faulkner, L. R., *Electrochemical Methods*, 2$^{nd}$ Ed., Wiley, New York, 2001
Barrena, E.; Ocal, C.; Salmeron, M., *J. Chem, Phys.*, 113: 2413-2418, 2000
Hamelin, A.; Vitanov, T.; Sevastyanov E; Popov A., *J. Electroanal. Chem.*, 145:225-264, 1983
Katz, E.; Willner, I., *Electroanalysis*, 15:913-947, 2003
Kittel, C., *Introduction to Solid State Physics*, 8$^{th}$ Ed., John Wiley & Sons, New York, 2005
Kotz, R.; Kolb, D. M.; Sass, J. K., *Surf Sci.*, 69:359-364, 1977
Kretschmann, E., *Z. Phys.*, 241:313-324, 1971
Kumar, A.; Biebuyck, H. A.; Whitesides, G. M., *Langmuir*, 10:1498-1511, 1994
McIntyre, J. D., *Surf Sci.*, 37:658-682, 1973
Orlowski, R.; Raether, H., *Surf. Sci.*, 54:303-308, 1976
Peterlinz, K. A.; Georgiadis, R., *Langmuir*, 12:4731-4740, 1996
Porter, M. D.; Bright, T. B.; Allara, D. L.; Chidsey, C. E. D., *J. Am. Chem. Soc.*, 109:3559-3568, 1987
Tao, N. J.; Boussaad, S.; Huang, W. L.; Arechabaleta, R. A.; D'Agnese, J., *Rev. Sci, Instrum.*, 70:4656-4660, 1999
Wang, S.; Boussaad, S.; Wong, S.; Tao, N. J., *Anal. Chem.*, 72:4003-4008, 2000

The invention claimed is:
1. A method of imaging surface impedance, comprising:
providing a sample block having a surface that is coated with a metal film;
disposing a solution in contact with the metal film;
providing a first electrode in contact with the solution and spaced apart from the metal film;

activating a light source configured to provide light that excites Surface Plasmon Resonance (SPR) of the metal film;

applying a modulated potential between the metal film and the first electrode;

capturing a sequence of images of the SPR of the metal film; and time correlating the sequence of images to the modulated potential to determine one or more electrical properties of the metal-solution interface that correspond to the response of the SPR of the metal film to the modulated potential.

2. The method of claim 1, further comprising:
generating an image of an amplitude component of the AC response of the SPR and an image of a phase component of the AC response of the SPR.

3. The method of claim 2, further comprising:
generating an image of the DC response of the SPR.

4. The method of claim 2, further comprising:
generating an image of the surface impedance of the metal film from the AC response of the SPR of the metal film to the modulated potential.

5. The method of claim 1, where the sample block is at least partially transparent to light from the light source.

6. The method of claim 5, where the SPR of the metal film is excited using a Kretschmann configuration or an Otto configuration.

7. The method of claim 1, where the metal film comprises an ordered pattern, and where the SPR of the metal film is excited using an optical grating configuration.

8. The method of claim 1, further comprising:
providing a second electrode in contact with the solution;
where, when applying the modulated potential, the first electrode acts as a reference electrode, the second electrode acts as a counter electrode, and the metal film acts as a working electrode.

9. The method of claim 1, where the modulated potential comprises an oscillating potential superimposed on a predetermined potential value.

10. The method of claim 1, where the sequence of images is captured with a charge-coupled device (CCD) detector or a complementary metal-oxide semonductor (CMOS) detector).

11. The method of claim 1, where an analyte is adsorbed on the metal film.

12. The method of claim 11, where the solution comprises the analyte and where the analyte adsorbs on the metal film from the solution.

13. The method of claim 11, where the analyte is selected from the group consisting of: cells, bacteria, and viruses.

14. The method of claim 1, where the solution comprises an electrolyte.

15. The method of claim 1, where applying the modulated potential comprises:
selecting a potential with a potentiostat; and
modulating the selected potential with a function generator.

16. An apparatus for imaging surface impedance, comprising:
a sample support configured to support a sample block having a surface that is coated with a metal film, the sample support configured to support a sample block such that a solution can be disposed in contact with the metal film of the sample block;
a light source configured to provide light that can excite Surface Plasmon Resonance (SPR) of the metal film of a supported sample block;
a first electrode configured to be disposed in contact with a solution and spaced apart from the metal film of a supported sample block;
a modulated potential source coupled to the first electrode and configured to be coupled to the metal film of a sample block such that the modulated potential source is activatable to provide a modulated potential between the metal film and the first electrode;
an imaging device configured to capture a sequence of images of SPR of the metal film of a supported sample block;
a processor coupled to the modulated potential source and to the imaging device, the processor configured to receive a sequence of images of SPR of the metal film of a supported sample block and to determine one or more electrical properties of the metal-solution interface that correspond to the response of the SPR of the metal film to the modulated potential by time correlating the sequence of images to the modulated potential.

17. The apparatus of claim 16, where the processor is further configured to generate an image of an amplitude component of the AC response of the SPR and an image of a phase component of the AC response of the SPR.

18. The apparatus of claim 17, where the processor is further configured to generate an image of the DC response of the SPR.

19. The apparatus of claim 17, where the processor is further configured to generate an image of the surface impedance of the metal film from the AC response of the SPR of the metal film to the modulated potential.

20. The apparatus of claim 16, where the sample block is at least partially transparent to light from the light source.

21. The apparatus of claim 20, where the apparatus is configured to support a sample block and to excite SPR of the metal film of a supported sample block in a Kretschmann configuration.

22. The apparatus of claim 20, where the apparatus is configured to support a sample block and to excite SPR of the metal film of a supported sample block in an Otto configuration.

23. The apparatus of claim 16, where the apparatus is configured to support a sample block on which the metal film comprises an ordered pattern, and where the apparatus is configured to excite SPR of the metal film of a supported sample block in an optical grating configuration.

24. The apparatus of claim 16, further comprising:
a second electrode coupled to the modulated potential source and configured to be disposed in contact with a solution and spaced apart from the metal film of a supported sample block;
where, if the modulated potential source is activated to apply a modulated potential between the first electrode and the metal film of a supported sample block, the first electrode acts as a reference electrode, the second electrode acts as a counter electrode, and the metal film acts as a working electrode.

25. The apparatus of claim 16, where the modulated potential source comprises a potentiostat configured to select the value of a modulated potential to be applied by the modulated potential source.

26. The apparatus of claim 25, where the modulated potential source comprises a signal generator to modulate the selected potential value.

27. The apparatus of claim 26, where the modulated potential source is configured to provide an oscillating potential superimposed on a selected potential value.

28. The apparatus of claim 16, where the light source comprises one or more light-emitting diodes (LEDs), lasers, or super-luminescence diodes (SLDs).

29. The apparatus of claim 16, where the imaging device comprises a charge-coupled device (CCD) detector or a complementary metal-oxide semonductor (CMOS) detector.

* * * * *

UNITED STATES PATENT AND TRADEMARK OFFICE
CERTIFICATE OF CORRECTION

| | |
|---|---|
| PATENT NO. | : 8,416,417 B2 |
| APPLICATION NO. | : 12/989617 |
| DATED | : April 9, 2013 |
| INVENTOR(S) | : Kyle James Foley et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 169 days.

Signed and Sealed this
Tenth Day of September, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,416,417 B2
APPLICATION NO. : 12/989617
DATED : April 9, 2013
INVENTOR(S) : Kyle James Foley et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 288 days.

This certificate supersedes the Certificate of Correction issued September 10, 2013.

Signed and Sealed this
Fifteenth Day of April, 2014

Michelle K. Lee
*Deputy Director of the United States Patent and Trademark Office*